(12) United States Patent
Lee et al.

(10) Patent No.: US 12,031,941 B2
(45) Date of Patent: Jul. 9, 2024

(54) METHODS TO AUTOMATICALLY CALIBRATE PH SENSORS WITHOUT SAMPLING

(71) Applicant: ERBI BIOSYSTEMS, INC., Stoneham, MA (US)

(72) Inventors: Harry Lee, Malden, MA (US); Kevin Shao-Kwan Lee, Arlington, MA (US)

(73) Assignee: EMD Millipore Corporation, Burlington, MA (US)

(*) Notice: Subject to any disclaimer, the term of this patent is extended or adjusted under 35 U.S.C. 154(b) by 569 days.

(21) Appl. No.: 16/992,054

(22) Filed: Aug. 12, 2020

(65) Prior Publication Data
US 2021/0048408 A1    Feb. 18, 2021

Related U.S. Application Data

(60) Provisional application No. 62/885,313, filed on Aug. 12, 2019.

(51) Int. Cl.
*G01N 27/416*    (2006.01)
*G01N 33/00*    (2006.01)
(Continued)

(52) U.S. Cl.
CPC ....... *G01N 27/4165* (2013.01); *G01N 33/004* (2013.01); *G05D 21/02* (2013.01); *G01D 18/008* (2013.01)

(58) Field of Classification Search
CPC .............. G01N 27/4163–4165; G01N 33/004; G05D 21/00–02; G01D 18/008
See application file for complete search history.

(56) References Cited

U.S. PATENT DOCUMENTS 5,763,760 A * 6/1998 Gumbrecht .......... A61B 5/1473
    73/1.06
6,123,827 A * 9/2000 Wong ................. G01N 33/4925
    204/415

(Continued)

FOREIGN PATENT DOCUMENTS

DE      10251183 A1 *  7/2003  ........... G01N 33/004
WO    2020/123524 A1     6/2020

OTHER PUBLICATIONS

Klinger, C., et al., "pH Sensor Recalibration Based on Exhaust CO2 Concentration for Bioprocess Transfer and Scaling, "Eppendorf (2018), Application Note, No. 363, pp. 1-6.

*Primary Examiner* — Joshua L Allen
*Assistant Examiner* — Vivian A Tran
(74) *Attorney, Agent, or Firm* — EMD Millipore Corporation

(57) ABSTRACT

Methods of calibrating a pH sensor fixed within an enclosed vessel are disclosed. The methods include introducing a buffer into the enclosed vessel, introducing a gas mixture comprising $CO_2$ into the enclosed vessel, measuring a pH signal of the solution, measuring a $CO_2$ concentration of a headspace gas of the solution, and calculating a pH value with a buffer calibration curve. The methods include calculating a calibration parameter with a sensor calibration curve and calibrating the pH sensor with the calibration parameter. Reactor systems are also disclosed. The systems include an enclosed reactor, a pH sensor, a $CO_2$ sensor, a temperature control subsystem, and a controller. Methods of facilitating pH sensor calibration without sampling in a bioreactor system are also disclosed. The methods include providing a controller and providing instructions to operably connect the controller to the pH sensor and the $CO_2$ sensor.

12 Claims, 7 Drawing Sheets

(51) Int. Cl.
  *G05D 21/02* (2006.01)
  *G01D 18/00* (2006.01)

(56) References Cited

U.S. PATENT DOCUMENTS

| | | |
|---|---|---|
| 9,176,060 B2 | 11/2015 | Lee et al. |
| 9,248,421 B2 | 2/2016 | Lee et al. |
| 9,328,962 B2 | 5/2016 | Lee et al. |
| 9,574,167 B2 | 2/2017 | Lee et al. |
| 2009/0220935 A1 | 9/2009 | Lee et al. |
| 2014/0234954 A1 | 8/2014 | Lee et al. |
| 2015/0132845 A1 | 5/2015 | Ram et al. |
| 2017/0059518 A1* | 3/2017 | Feng ............... C12M 41/26 |
| 2018/0216059 A1* | 8/2018 | Eisenkraetzer ...... G05D 21/02 |

* cited by examiner

METHODS TO AUTOMATICALLY CALIBRATE PH SENSORS WITHOUT SAMPLING

CROSS-REFERENCE TO RELATED APPLICATIONS

This application claims priority under 35 U.S.C. § 119(e) to U.S. Provisional Patent Application No. 62/885,313 titled "Methods to Automatically Calibrate pH Sensors without Sampling" filed Aug. 12, 2019, the entire disclosure of which is herein incorporated by reference in its entirety for all purposes.

FIELD OF TECHNOLOGY

Aspects and embodiments disclosed herein relate to systems and methods for measuring pH of a sample. In particular, aspects and embodiments disclosed herein relate to systems and methods for measuring pH and calibrating pH sensors in a sterile environment.

SUMMARY

In accordance with one aspect, there is provided a method of calibrating a pH sensor fixed within an enclosed vessel. The method may comprise introducing a buffer into the enclosed vessel at a controlled temperature. The method may comprise sequentially introducing a gas mixture comprising $CO_2$ into the enclosed vessel to form gas mixture and buffer solutions having variable concentrations of $CO_2$. The method may comprise measuring a pH signal of each solution with the pH sensor and a $CO_2$ concentration of a headspace gas of each solution. The method may comprise calculating a pH value for each solution from the $CO_2$ concentration with a calibration curve for the buffer. The method may comprise calculating a calibration parameter for the pH sensor from the pH signal and the respective pH value for each solution with a calibration curve for the pH sensor. The method may comprise calibrating the pH sensor with the calibration parameter.

In some embodiments, the method may comprise measuring a pH signal of at least four solutions and a $CO_2$ concentration of the headspace gas of the at least four solutions, calculating at least four respective pH values, and calculating the calibration parameter for the pH sensor from the at least four pH signals and the at least four respective pH values.

The method may comprise measuring the pH signal with the pH sensor and the $CO_2$ concentration after the solution reaches equilibrium.

The method may further comprise generating the calibration curve for the buffer.

In some embodiments, the calibration curve for the buffer is in the form of:

$$pH_{fit} = A + B^* \log_{10}(C + CO_{2perc})$$

where A, B, and C are fitting parameters and $CO_{2perc}$ is the measured $CO_2$ concentration as a percentage of the headspace gas total composition.

The method may comprise calculating the fitting parameters A, B, and C by sequentially introducing a stable mixture of $CO_2$ and air into the buffer at a controlled temperature to form stable mixture and buffer combinations, measuring a pH signal of the combination and a $CO_2$ concentration of a headspace gas of the combination, fitting the pH signal and the $CO_2$ concentration in the calibration curve formula, and determining the fitting parameters A, B, and C which produce lowest least squares error between the fitted pH value, $pH_{fit}$, and the measured pH signal.

The method may comprise measuring the pH signal of the combination and the $CO_2$ concentration of the headspace gas of the combination after the combination reaches equilibrium.

In some embodiments, the calibration curve for the pH sensor is in the form of:

$$pH_{sensor} = (\log_2(S-W) - \log_2(X-S))^* Y + Z,$$

where W, X, Y, and Z are fitting parameters and S is the pH signal.

The method may comprise calculating the fitting parameters W, X, Y, and Z by fitting the pH signal and the pH value in the calibration curve formula and determining the fitting parameters W, X, Y, and Z which produce lowest least squares error between the fitted pH value, $pH_{sensor}$, and the measured pH signal.

In some embodiments, the method may comprise introducing a humidification solution into the vessel in an amount effective to compensate for evaporation of the buffer.

In some embodiments, the buffer may be controlled to a predetermined temperature between 30° C. and 39° C.

The enclosed vessel may be sterile. The method may comprise sterilizing the enclosed vessel by at least one of steam sterilization, autoclave sterilization, gamma irradiation, e-beam irradiation, and ethylene oxide sterilization.

In some embodiments, the enclosed vessel may be a bioreactor, for example, a microbioreactor.

In accordance with another aspect, there is provided a reactor system. The reactor system may comprise an enclosed reactor fluidly connectable to a source of a buffer. The system may comprise a pH sensor positioned to measure pH of a fluid within the reactor. The system may comprise a $CO_2$ sensor positioned to measure $CO_2$ concentration within the reactor. The system may comprise a temperature control subsystem configured to control temperature of the fluid within the reactor. The system may comprise a controller operably connected to the pH sensor and the $CO_2$ sensor. The controller may be configured to calculate a pH value from a $CO_2$ concentration measurement obtained by the $CO_2$ sensor with a calibration curve for the buffer. The controller may be configured to calculate a calibration parameter for the pH sensor from a pH signal obtained by the pH sensor and the pH value with a calibration curve for the pH sensor. The controller may be configured to calibrate the pH sensor with the calibration parameter.

In some embodiments, the enclosed reactor may be a microbioreactor.

In some embodiments, the enclosed reactor may be sterile.

In some embodiments, the enclosed reactor may be fluidly connectable to a source of a humidification solution.

In some embodiments, the $CO_2$ sensor may be positioned to measure $CO_2$ concentration of a headspace gas within the enclosed reactor.

The controller may be operably connected to at least one of the source of the buffer and the source of the gas mixture. The controller may be configured to introduce at least one of the buffer and the gas mixture into the enclosed reactor.

The controller may be operably connected to the temperature control subsystem.

The controller may be operably connected to the source of the humidification solution. The controller may be configured to introduce the humidification solution into the enclosed reactor.

The controller may be configured to calculate parameters A, B, and C in the calibration curve for the buffer having a formula in the form of:

$$pH_{fit}=A+B*\log_{10}(C+CO_{2perc})$$

where A, B, and C are fitting parameters and $CO_{2perc}$ is the measured $CO_2$ concentration as a percentage of the headspace gas total composition.

The controller may be configured to calculate parameters W, X, Y, and Z in the calibration curve for the pH sensor having a formula in the form of:

$$pH_{sensor}=(\log_2(S-W)-\log_2(X-S))*Y+Z,$$

where W, X, Y, and Z are fitting parameters and S is the pH sensor signal.

In accordance with another aspect, there is provided a method of facilitating pH sensor calibration without sampling in a bioreactor system. The bioreactor system may comprise an enclosed bioreactor, a pH sensor positioned to measure pH of a fluid within the bioreactor, and a $CO_2$ sensor positioned to measure $CO_2$ concentration within the bioreactor. The method may comprise providing a controller configured to calculate a pH value from a $CO_2$ concentration obtained by the $CO_2$ sensor with a calibration curve for the buffer, calculate a calibration parameter for the pH sensor from a pH signal obtained by the pH sensor and the pH value with a calibration curve for the pH sensor, and calibrate the pH sensor with the calibration parameter. The method may comprise instructing a user to operably connect the controller to the pH sensor. The method may comprise instructing a user to operably connect the controller to the $CO_2$ sensor.

The method may comprise operably connecting the controller to the pH sensor. The method may comprise operably connecting the controller to the $CO_2$ sensor.

The method may comprise providing at least one of the pH sensor and the $CO_2$ sensor.

In some embodiments, the method may comprise programming the controller.

Still other aspects, embodiments, and advantages of these exemplary aspects and embodiments, are discussed in detail below. Moreover, it is to be understood that both the foregoing information and the following detailed description are merely illustrative examples of various aspects and embodiments and are intended to provide an overview or framework for understanding the nature and character of the claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
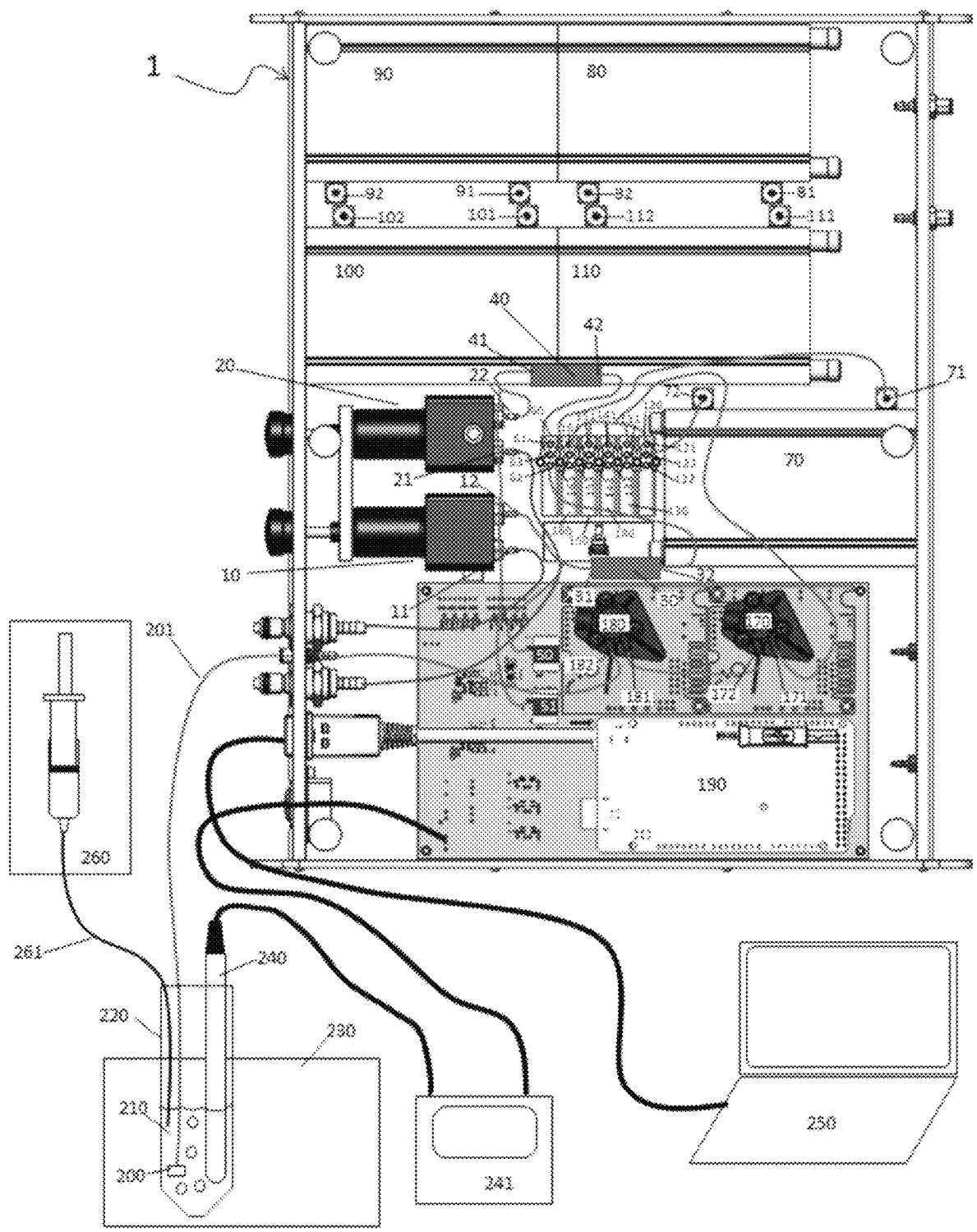
FIG. 1 is a schematic diagram of a system, according to one embodiment.

In chemistry, pH is the scale of acidity or basicity of a sample. The pH of a sample is typically measured to monitor or control a number of parameters of the sample. For example, in biochemistry, pH value of a cell culture sample may be measured to monitor viability and metabolic activity of the cells.

Cell culture is a process by which cells are maintained under controlled conditions, generally in a foreign environment. Cells may be maintained, grown, activated, or transduced under controlled conditions. Conditions may vary for each process and by cell type. General cell culture practices include monitoring and controlling the conditions, such as pH and temperature, of the cell culture.

For instance, treating cells at high cell density may generally include monitoring cell metabolic activity through physiochemical sensor measurements or controller responses. In general, the signal strength of concentration dependent parameters such as pH, dissolved oxygen, or carbon dioxide may be much larger at high cell density. In some embodiments, cell metabolic activity may be monitored by monitoring and controlling pH of the media. Changes in pH controller output may be used to infer metabolic activity of the cells. Changes in pH may be measured by pH sensor or carbon dioxide or base demand of the perfusion chamber. Such monitored changes may be used in a feedback mechanism to trigger downstream or additional steps in a treatment protocol. Thus, there is a need for accurate pH measurement in a cell culture protocol. In particular, pH sensors must be calibrated to obtain accurate readings of pH.

Calibration of a pH sensor is typically performed by measuring a signal from the pH sensor when placed in a few standard pH buffers and then fitting the signal against pH of the standard buffers. For a typical pH electrode, the signal may comprise the electrode voltage and calibration may involve correcting for the pH offset and slope of the response, accounting for the temperature. For dye-based pH sensors where the protonated and deprotonated molecule has different optical properties, a number of signal and pH measurements are typically made until there is sufficient data to generate a curve fit. In such instances, the signal is typically a ratio of absorptions or fluorescence, R, at two different wavelengths and the calibration curve is typically of the form:

$$[\log(R-R_{min})-\log(R_{max}-R)]*D+K$$

where the four parameters to fit are $R_{min}$, $R_{max}$, D, and K.

Performing this calibration procedure is straightforward when only a few pH sensors need to be calibrated, or for many pH sensors if the sensors can all be calibrated together by immersing the plurality in the same container for calibration with standard buffers. However, the procedure becomes more difficult when each pH sensor is isolated and/or sterility must be maintained. For example, pH sensors within bioreactors are generally difficult to calibrate.

For large bioreactors, pH sensors are typically calibrated prior to steam sterilization with standard buffers. The sterilization process can affect the calibration. A single point recalibration is typically performed by taking a culture medium sample from the bioreactor and measuring pH of the sample with another calibrated pH sensor. For a known calibration error form, such as a pure offset error or a slope error, the calibration can be corrected. However, the recalibration method is vulnerable to errors arising from the temperature differential between the sample and the culture medium inside the bioreactor and $CO_2$ outgassing from the sample, each of which may result in pH drift.

One conventional method to overcome the problems described above involves employing the equilibrium between $CO_2$, pH, pressure, and temperature to correlate exhaust $CO_2$ measurements with internal pH. The exhaust $CO_2$ may be measured with a $CO_2$ gas analyzer. Comparing $CO_2$ exhaust measurements and pH measurements in bioreactors using fresh culture media may be used to detect calibration errors in pH electrodes and also make corrections to the calibrations. However, this method may generally not be employed to automatically perform primary calibrations on pH sensors permanently fixed within bioreactors or correct pH calibrations after cell growth has occurred.

For single use bioreactor devices (such as bag based, vessel based, or microfluidic integrated bioreactors) pH is typically measured with a dye-based pH sensor, for which the optical properties of the dye identify pH of the sample. Measurement of the optical properties of the dye is sensitive to sterilization procedures such as gamma irradiation, e-beam irradiation, ethylene oxide sterilization, and other sterilization methods. Thus, the dye-based pH sensors must be calibrated by direct primary calibration for accurate pH measurement. Calibration of dye-based pH sensors is conventionally performed by introducing fluids with known pH into these vessels and measuring the signal to determine any offset. Conventional calibration may also be performed by introducing a fluid with a stable pH into the vessel, measuring the signal, then comparing the signal to an externally measured pH. For a large number of bioreactors, performing the conventional calibration operations is labor intensive or requires the use of robotic automation.

There is a need for automatically calibrating pH sensors in bioreactor devices, for example, sterile and/or single use bioreactor devices.

While embodiments described herein generally refer to cell treatment systems, such as cell culture systems and gene modified cell therapies, such an application is exemplary. It should be understood that the systems and methods disclosed may be employed for calibration of a pH sensor related to any enclosed vessel. For example, the systems and methods disclosed may be employed for calibration of a pH sensor related to any enclosed vessel which is configured to maintain controlled conditions, for example, sterile conditions.

In accordance with one aspect, there is provided a method of calibrating a pH sensor. The systems and methods disclosed herein may generally be employed for calibration of a pH sensor fixed within a vessel, optionally after sterilization of the vessel and sensor assembly. The systems and methods may be capable of automatic single point calibration of the fixed pH sensor.

The methods of pH sensor calibration may generally comprise generating a calibration curve relating $CO_2$ to pH of a buffer fluid, introducing the buffer fluid into a vessel, and calibrating the pH sensor using the calibration curve.

The calibration curve may be in the form of:

$$pH_{fit}=A+B*\log_{10}(C+CO_{2perc})$$

where A, B, and C are fitting parameters and $CO_{2perc}$ is measured $CO_2$ concentration as a percentage of total gas composition.

The A, B, and C values for a selected buffer fluid may be obtained by bubbling a number of stable mixtures of $CO_2$ and air through the buffer fluid at a known temperature, measuring $CO_2$ concentration with one or more $CO_2$ sensors, and measuring pH with a pH sensor after equilibrium is reached for each stable mixture. In an exemplary embodiment, a calibration curve for a bicarbonate-based buffer was generated by bubbling the $CO_2$ and air mixture through the buffer at a temperature between 30° C. and 39° C., (about 37° C.), using two $CO_2$ sensors to measure $CO_2$, and using a standard pH electrode as the pH sensor. The resulting measured $CO_2$ concentration and pH pairs were then used to fit a calibration formula for the buffer, as shown above. The parameters A, B, and C that produced the lowest least squares error between the fitted pH, $pH_{fit}$, and measured pH may be selected for the calibration formula, to be used to infer the pH of the buffer fluid when the vessel pH sensors were calibrated.

The method may comprise performing an internal pH sensor calibration. The internal pH sensor calibration may comprise introducing the buffer into the vessel, controlling temperature of the buffer, equilibrating the buffer sequentially with a plurality of $CO_2$ concentrations, and measuring a corresponding pH signal with the pH sensor for each $CO_2$ concentration. In an exemplary embodiment, the bicarbonate based buffer was introduced into the vessel, controlled to a temperature between 30° C. and 39° C., (about 37° C.), the buffer was equilibrated sequentially with four $CO_2$ concentrations, and the corresponding pH signal for each $CO_2$ concentration was measured with the internal pH sensor. The method may comprise calculating pH of the buffer fluid using the calibration curve above fitted with parameters A, B, and C that produced the lowest least squares error.

The method may comprise using the internal pH sensor signals and calculated pH values to fit a sensor formula of the form:

$$pH_{sensor}=(\log_2(S-W)-\log_2(X-S))*Y+Z,$$

where S is the pH sensor signal and W, X, Y, and Z are fitting parameters.

The parameters W, X, Y, and Z that produced the lowest least squares error between the fitted pH, $pH_{sensor}$, and measured pH may be selected for the calibration formula, to be used to calibrate the pH sensor. The method may comprise calibrating the pH sensor with the calibration parameters.

Thus, in general, the methods of calibrating a pH sensor may comprise introducing a buffer into the enclosed vessel at a controlled temperature, introducing a gas mixture comprising $CO_2$ into the enclosed vessel to form a gas mixture and buffer solution, and measuring a pH signal with the pH sensor to be calibrated and a $CO_2$ concentration of the headspace gas of the solution. The method may comprise repeating the gas mixture and buffer solution steps to obtain an array of pH signal and $CO_2$ concentration data points. The method may comprise calculating a pH value from the measured $CO_2$ concentration with a calibration curve for the buffer. The calibration curve for the buffer may be previously generated, or the method may comprise generating the calibration curve as described in more detail below.

The method may comprise obtaining an array of pH signal and $CO_2$ concentration data points by producing gas mixture and buffer solutions having variable $CO_2$ concentrations. In general, the method may comprise producing and measuring more than one gas mixture and buffer solution. In some embodiments, the method may comprise producing and measuring at least two gas mixture and buffer solutions, for example, at least four solutions, at least six solutions, at least eight solutions, at least ten solutions, or more. The method may comprise producing and measuring as many gas mixture and buffer solutions as necessary to obtain a desired confidence level (for example at least 90% or at least 95% confidence).

The variable $CO_2$ concentration may be achieved by introducing a gas mixture having a different composition of $CO_2$ or by introducing a gas mixture having a fixed concentration of $CO_2$ in more than one discrete amount to a fixed volume of buffer. For example, a second volume of the gas mixture may be introduced after a first volume and the buffer reach equilibrium, effectively increasing $CO_2$ concentration of the solution. In some embodiments, the methods may comprise combining $CO_2$ with a fixed gas mixture to produce the variable $CO_2$ concentration gas mixtures.

In certain embodiments, the method may comprise allowing the solution to reach equilibrium before measuring the pH signal and the $CO_2$ concentration of the equilibrium gas. In the systems and methods disclosed herein, equilibrium may generally refer to the state in which both reactants (here, the gas mixture and the buffer) and products (here, the mixed solution) are present in concentrations which have substantially no further tendency to change with time, so that there is substantially no observable change in the properties of the mixture. Thus, allowing the solution to reach equilibrium before measuring the pH signal and the $CO_2$ concentration may produce data sets with greater accuracy.

The method may comprise measuring $CO_2$ concentration of the headspace gas of the solution. In general, measuring $CO_2$ concentration of the headspace may be performed by a gas analyzer. In sterile environments, a gas analyzer may be more accurate than a liquid $CO_2$ sensor. However, the method may alternatively or additionally comprise measuring a dissolved $CO_2$ concentration of the solution to obtain the $CO_2$ percent of the equilibrium solution with similar results. In such a method, the liquid $CO_2$ sensor may be externally calibrated.

The method may comprise calculating a calibration parameter for the pH sensor from the pH signal and the respective pH value calculated with the buffer calibration curve. The calibration parameter may be calculated with a calibration curve for the pH sensor. The method may comprise calibrating the pH sensor with the calibration parameter.

The array of pH signal and $CO_2$ concentration data points may be used to generate a respective set of pH value data points. Thus, in some embodiments, more than one, at least two, at least four, at least six, at least eight, at least ten, or more respective data points may be used to determine the fitting parameters for the buffer calibration curve (for example, A, B, and C as described above) and the fitting parameters for the calibration curve (for example, W, X, Y, and Z as described above).

In certain embodiments, the method may comprise generating the buffer calibration curve. The buffer calibration curve may be generated by combining the buffer and a gas mixture comprising $CO_2$ (for example, a stable mixture of $CO_2$ and air) at a controlled temperature to form a gas mixture and buffer combination, and measuring a pH signal and a $CO_2$ concentration of the combination. In some embodiments, the calibration curve may be generated within the enclosed vessel, for example, with the pH sensor to be calibrated. In other embodiments, the calibration curve may be previously generated or generated externally. The method may comprise repeating the gas mixture and buffer solution steps to obtain an array of pH signal and $CO_2$ concentration data points. The method may comprise allowing the combination to reach equilibrium before measuring the pH signal and the $CO_2$ concentration of the equilibrium combination. The method may comprise fitting the pH signal and $CO_2$ concentration data points to the buffer calibration curve, as previously described.

The methods disclosed herein may comprise introducing a buffer fluid into a vessel. The buffer fluid may be any fluid that has a pH dependent on $CO_2$ concentration. For example, the buffer fluid may comprise bicarbonate or a salt of bicarbonate. The buffer fluid may be a bicarbonate-based buffer fluid. In certain embodiments, the buffer may be a biocompatible buffer. The buffer may comprise a biological buffering agent. Exemplary biocompatible buffer fluids include cell culture media comprising bicarbonate or a salt of bicarbonate. For example, the biocompatible buffer may comprise cell culture media and sodium bicarbonate. The cell culture media may be one commonly used to culture animal or human cells.

The systems and methods disclosed herein may refer to an enclosed vessel. The enclosed vessel may generally be a vessel having at least one inlet for the buffer and at least one inlet for the gas mixture, which is otherwise sealed. In some embodiments, the enclosed vessel seal may be a hermetic seal. In particular embodiments, the enclosed vessel may be a bioreactor or a microbioreactor. However, any enclosed vessel may be used for the methods disclosed herein. Specifically, any enclosed vessel configured to maintain controlled conditions within the vessel may be used for the methods disclosed herein.

In some embodiments, the controlled conditions include sterility. The systems and methods disclosed herein may comprise using a sterile vessel. The methods disclosed herein may comprise sterilizing the vessel. The sterilization method may include steam sterilization, autoclave sterilization, gamma irradiation, e-beam irradiation, ethylene oxide sterilization, and other sterilization methods. The method may comprise maintaining sterility of the enclosed vessel during the calibration process. Thus, the method may comprise introducing a sterile buffer. The buffer may be sterilized by methods recognized in the art, for example, sufficient for particular conditions such as cell culture. The methods disclosed herein allow calibration of a pH sensor within a sterile enclosed vessel without compromising sterility of the system.

In some embodiments, fluid may be added to the vessel to compensate for evaporation during bubbling or during combination of the buffer and gas mixture. The fluid may be added in an amount effective to compensate for the evaporation. The fluid may comprise water or buffer. In some embodiments, the fluid may be a humidification solution, having a composition effective to replace the evaporated buffer, for example, without altering the total composition of the buffer within the reactor.

The methods disclosed herein may comprise controlling temperature of the buffer fluid. Variation in temperature may generally have an effect on pH of a sample. Thus, the methods may generally comprise controlling temperature to maintain correlation of the pH signals and calculated pH values between samples. Temperature may be controlled to be within a predetermined range. The predetermined range may span, for example, ±0.5° C., ±1° C., ±2° C., ±3° C., ±4° C., or ±5° C.

In certain embodiments, the temperature may be controlled to a physiological temperature. Thus, the predetermined temperature may be selected to be between 30° C. and 39° C. For example, the predetermined temperature range may be between 34° C. and 39° C., between 35° C. and 38° C., between 36° C. and 39° C., between 36° C. and 38° C., between 36.5° C. and 37.5° C., about 36° C., about 37° C., or about 38° C.

The methods disclosed herein may be employed for cell culture or treatment. In certain exemplary embodiments, methods of cell culture or treatment may comprise controlling pH of media to monitor and/or control cell metabolic state. In such embodiments, the methods may comprise introducing an effective amount of an additive comprising a pH control agent. The method may comprise controlling pH of the media within the perfusion chamber to a pH value of between about 6.0 and 8.5, for example, between about 6.8 and about 7.4. The methods may comprise controlling pH to a substantially physiological pH value. In some embodiments, the pH control agent may be a base. In some embodiments, the pH control agent may be an acid. The pH control agent may comprise, for example, sodium hydroxide, sodium carbonate, sodium bicarbonate, ammonia, potassium hydroxide, carbon dioxide, hydrochloric acid, or phosphoric acid.

For example, while not wishing to be bound by theory, it is believed that cell activation for a high-density culture (for example, more than 2×10$^6$ cells/mL) causes a large change in media pH due to the increase in cellular metabolism. Maintaining the pH at acceptable levels (for example, between approximately 6.9 and 7.3 for T-cells) may be essential for cell growth and viability during unit operations where high cell density is advantageous, such as cell transduction, and cell expansion. Perfusion flow may counteract the metabolic byproducts (typically acidic in nature but may be basic) generated by the cells. For instance, perfusion flow may control or reduce the change or decrease in pH compared to batch cultures.

In some embodiments, the method may further comprise measuring at least one parameter of the media. The at least one parameter may be selected from optical density, dissolved oxygen concentration, temperature, and light scattering. The at least one parameter may inform of the need to perform a pH calibration process, as described herein. Thus, in some embodiments, the method may comprise initiating a pH calibration process responsive to the measurement of the at least one parameter.

In accordance with another aspect, there is provided a system for calibrating a pH sensor in a controlled environment. The system may be capable of calibrating the pH sensor without compromising integrity of the controlled environment and without sampling the solution within the controlled environment.

The system may comprise an enclosed reactor fluidly connectable to a source of a buffer, a pH sensor positioned to measure pH of a fluid within the reactor, a $CO_2$ sensor positioned to measure $CO_2$ concentration within the reactor, and a controller.

In some embodiments, the system may further comprise a temperature control subsystem configured to control temperature of the fluid within the reactor. In some embodiments, the temperature control subsystem may be in thermal communication with the vessel. In some embodiments, the temperature control subsystem may be in thermal communication with the source of the buffer. In some embodiments, the temperature control subsystem may be in thermal communication with the source of the gas mixture.

The pH sensor may be a pH electrode, an optical pH sensor, or a dye-based pH sensor. In some embodiments, the pH sensor may be any sensor capable of sterilization. The pH sensor may be accurate at temperatures up to 42° C. The pH sensor may have an accuracy within about 0.1 pH units or within about 0.01 pH units. In some embodiments, the pH sensor may comprise a plurality of pH sensors, for example, two or more pH sensors.

The $CO_2$ sensor may have a lower detection limit of at least about 5 ppb. The $CO_2$ sensor may have an upper detection limit of greater than about 500 ppm. In some embodiments, the $CO_2$ sensor may be a gas analyzer positioned to measure $CO_2$ concentration in a headspace of the enclosed vessel. The gas analyzer may be capable of monitoring other gasses, in addition to $CO_2$. For example, the gas analyzer may be capable of monitoring $O_2$, $N_2$, $N_2O$, HF, CO, $H_2O$, $CH_4$, and combinations thereof in various ranges. The $CO_2$ sensor may be accurate at temperatures up to 42° C. In some embodiments, the $CO_2$ sensor may be a liquid $CO_2$ sensor positioned to measure $CO_2$ in a solution within the enclosed vessel. The liquid $CO_2$ sensor may be calibrated by external calibration. In some embodiments, the $CO_2$ sensor may comprise a plurality of $CO_2$ sensors, for example, two or more $CO_2$ sensors.

The controller may be operably connectable to the pH sensor and the $CO_2$ sensor. The controller may be configured to calculate a pH value from a $CO_2$ concentration measurement obtained by the $CO_2$ sensor with a calibration curve for the buffer, as previously described. The controller may be configured to calculate a calibration parameter for the pH sensor from a pH signal obtained by the pH sensor and the pH value with a calibration curve for the pH sensor, as previously described. The controller may be configured to calibrate the pH sensor with the calibration parameter, as previously described.

The controller may be a computer or mobile device. The controller may comprise a touch pad or other operating interface. For example, the controller may be operated through a keyboard, touch screen, track pad, and/or mouse. The controller may be configured to run software on an operating system known to one of ordinary skill in the art. The controller may be electrically connected to a power source. The controller may be digitally connected to the one or more components. The controller may be connected to the one or more components through a wireless connection. For example, the controller may be connected through wireless local area networking (WLAN) or short-wavelength ultrahigh frequency (UHF) radio waves. The controller may further be operably connected to any pump or valve within the system, for example, to enable the controller to direct fluids or additives as needed. The controller may be coupled to a memory storing device or cloud-based memory storage.

Multiple controllers may be programmed to work together to operate the system. For example, a controller may be programmed to work with an external computing device. In some embodiments, the controller and computing device may be integrated. In other embodiments, one or more of the processes disclosed herein may be manually or semi-automatically executed.

The temperature control subsystem may comprise a temperature sensor. The temperature control subsystem may comprise a heater configured to maintain temperature of the fluid. In some embodiments, the temperature control subsystem may comprise a cooling unit configured to maintain temperature of the fluid.

The system may comprise a source of the humidification solution fluidly connected to the enclosed reactor. In some embodiments, the temperature control subsystem may be in thermal communication with the source of the gas mixture.

Figure 7:
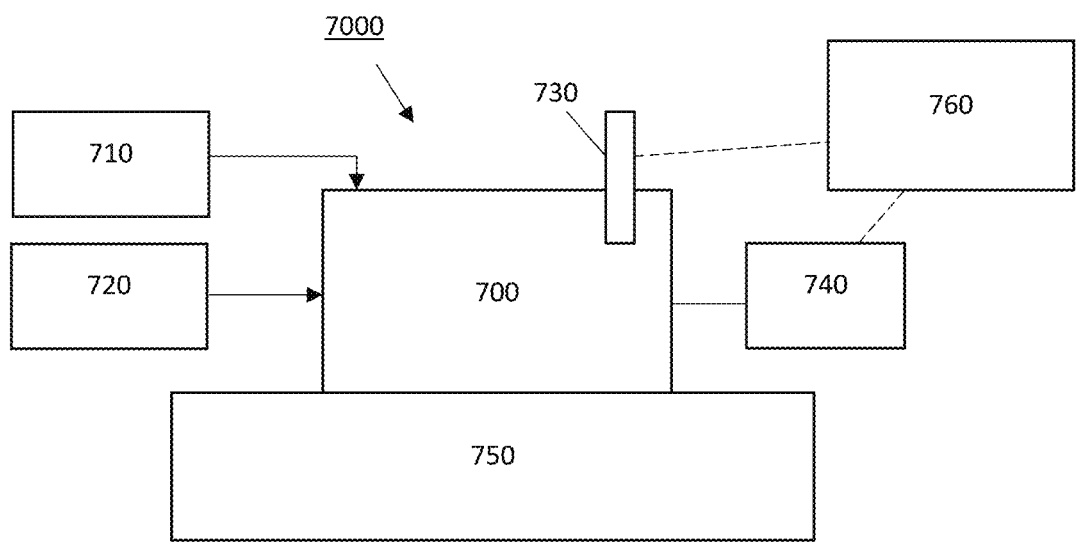
FIG. 7 is a box diagram of a system, according to one embodiment.

FIG. 7 is a box diagram of an exemplary system 7000. In FIG. 7, exemplary system 7000 comprises enclosed vessel 700, the source of a buffer 710, the source of a gas mixture 720, pH sensor 730 positioned to measure pH of a fluid within the vessel 700, a $CO_2$ sensor 740 positioned to measure $CO_2$ concentration within the reactor 700, temperature control subsystem 750 configured to control temperature of the fluid within the reactor 700, and controller 760.

The enclosed vessel may be any enclosed vessel. In some embodiments, the enclosed vessel may be a chemical reactor. The enclosed vessel may be formed of a material inert to the selected chemical reactants. The enclosed vessel may be a bioreactor. The bioreactor may be formed of a biocompatible material. In some embodiments, the enclosed vessel may be a microbioreactor. The enclosed vessel may generally be formed of a material inert to the buffer. The enclosed vessel may generally be formed of a material inert to $CO_2$ gas and, optionally, substantially impermeable to $CO_2$ gas.

In certain exemplary embodiments, the vessel may be a perfusion chamber. The perfusion chamber may be formed or lined with a material inert to the cells and cell treatment additives disclosed herein. The system and/or perfusion chamber may have one or more embodiments as described in any one or more of International Patent Application Publication No. WO2020/123524 titled "Methods of Manufacturing Cell Based Products Using Small Volume Perfusion Processes," filed on Dec. 10, 2019; U.S. Pat. No. 9,328,962 titled "Apparatus and methods to operate a microreactor," filed on Jan. 25, 2013; U.S. Patent Application Publication No. 2014/0234954 titled "Methods and apparatus for independent control of product and reactant concentrations," filed on Feb. 14, 2014; U.S. Pat. No. 9,176,060 titled "Apparatus and methods to measure optical density," filed on Apr. 9, 2012; and U.S. Pat. No. 9,248,421 titled "Parallel integrated bioreactor device and method," filed on Oct. 10, 2006, each of which is herein incorporated by reference in their entireties for all purposes.

Figure 8:
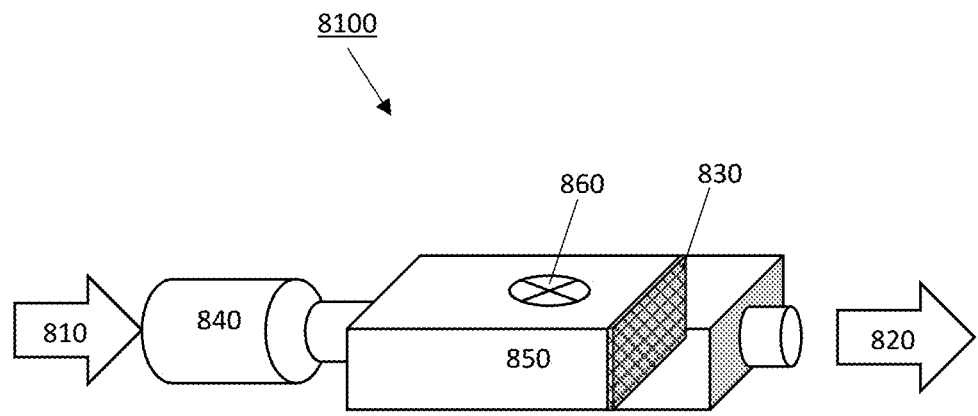
FIG. 8 is a schematic diagram of a microbioreactor, according to one embodiment.

An exemplary perfusion chamber 8100 is shown in FIG. 8. The exemplary perfusion chamber 8100 includes at least one inlet 810, at least one outlet 820, at least one filter 830, and internal chamber 850. The exemplary perfusion chamber 8100 includes at least one check valve 840, which may be a pneumatic valve, positioned at the at least one inlet 810 to substantially isolate the contents of the internal chamber 850 when actuated. The exemplary perfusion chamber 8100 includes at least one port 860 for fluid communication with the internal chamber 850. The at least one port 860 may be used as an access port for a sensor. As previously described, the perfusion chamber may comprise a plurality of inlets 810, outlets 820, filters 830, valves 840, and ports 860 as necessary.

The system may comprise a source of cells fluidly connectable, and in use fluidly connected, to the perfusion chamber. The cells may be suspended in a media, for example, a cell culture media. The media may comprise one or more nutrient or additive in an amount effective to maintain viability of the cells. The source of the cells may comprise any cells and/or cell density as previously described.

The system may comprise a source of an additive fluidly connectable, and in use fluidly connected, to the perfusion chamber. The additive may be in aqueous, particle, or gel form. The additive may be in any form suitable for combination with the cells within the perfusion chamber. In exemplary embodiments, the additive may comprise one or more of cell culture media, a transducing agent, a pH control agent, and a cell activator. In general, any nutrient, agent, or additive disclosed herein may be fluidly connectable or connected to the perfusion chamber. For embodiments comprising more than one additive fluidly connectable to the perfusion chamber, each additive may be independently fluidly connectable or connected to the perfusion chamber. In other embodiments, one or more additives may be combined, and the combination may be fluidly connectable or connected to the perfusion chamber.

The system may additionally comprise at least one sensor selected from an optical density sensor, a dissolved oxygen sensor, a temperature sensor, and a light scattering sensor fluidly connected to the perfusion chamber. Thus, the at least one sensor may be configured to measure at least one parameter of the cells or the media selected from optical density, dissolved oxygen concentration, temperature, and light scattering, respectively. The at least one sensor may be an in-line sensor positioned at an inlet or outlet of the perfusion chamber. The at least one sensor may be positioned at least partially within the perfusion chamber. Any sensor positioned partially within the perfusion chamber may be introduced through an otherwise hermetically sealed inlet or integrated into the perfusion chamber.

In some embodiments, the controller may be operatively connected to the at least one sensor, for example, optical density, dissolved oxygen concentration, temperature, or light scattering sensor. The controller may be configured to initiate a pH calibration sequence or notify a user of the need to initiate a pH calibration sequence responsive to the at least one optical density, dissolved oxygen concentration, temperature, or light scattering measurement.

Figure 9:
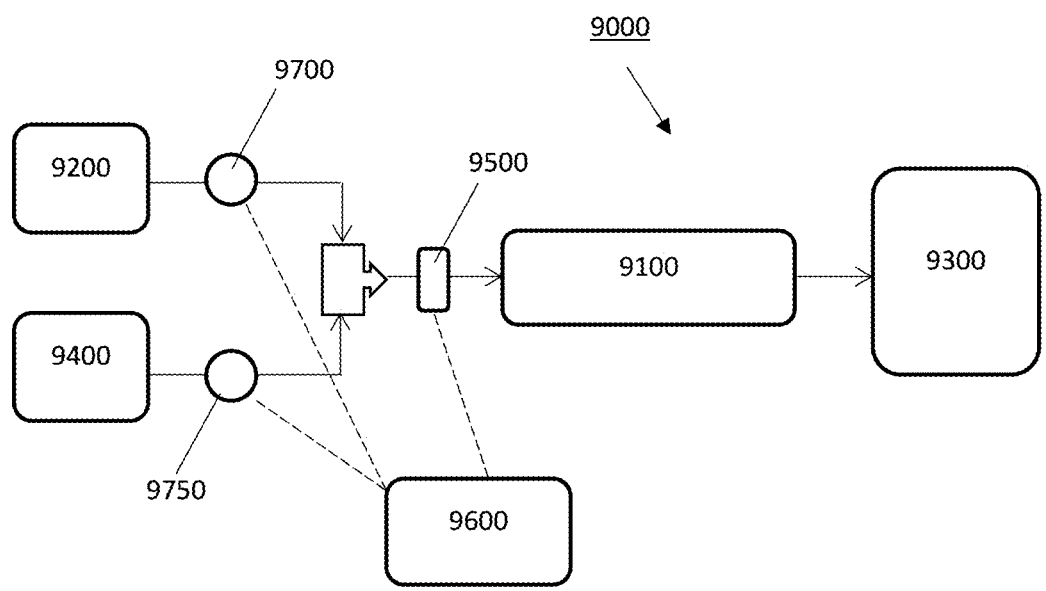
FIG. 9 is a schematic diagram of a microbioreactor system, according to one embodiment.

An exemplary system for treating cells 9000 is shown in FIG. 9. The exemplary system 9000 includes a perfusion chamber 9100 as shown in FIG. 8. The perfusion chamber 9100 is fluidly connected to a source of cells 9200 and a waste chamber 9300. The perfusion chamber 9100 is fluidly connected to at least one source of an additive 9400. The system includes at least one sensor 9500. While sensor 9500 is shown positioned and configured to measure a parameter of the suspension upstream from the perfusion chamber 9100, it should be understood that the system 9000 may include a plurality of sensors 9500 and/or the sensor 9500 may be positioned and configured to measure a parameter of the suspension within the perfusion chamber 9100, upstream from the perfusion chamber 9100, and/or downstream from the perfusion chamber 9100. In particular, although not shown, system 9000 may include at least one pH sensor and at least one $CO_2$ sensor (for example, a gas analyzer) positioned to measure pH and $CO_2$, respectively, within the perfusion chamber 9100, as previously described with respect to FIG. 7.

The system 9000 includes controller 9600 operatively connected to the at least one sensor 9500. The system 9000 includes pump 9700 positioned and configured to direct cells in media from the source of cells 9200 to the perfusion chamber 9100. The system 9000 includes pump 9750 positioned and configured to direct additive from the source of the additive 9400 to the perfusion chamber 9100. Pumps 9700, 9750 may be operatively connected to the controller 9600.

In accordance with another aspect, there is provided a method of facilitating cell therapy. The method may comprise providing one or more components of a system for performing cell culture, as previously described. For example, the method may comprise providing a perfusion chamber, at least one sensor, and/or a controller. The method may comprise instructing a user to operatively connect the controller to the at least one sensor and/or to one or more valves or pumps within the system configured to direct fluids. The method additionally may comprise instructing a user or operator to fluidly connect the perfusion chamber to a source of cells and/or a source of an additive, as previously described.

In certain embodiments, the method may comprise programming the controller to operate in accordance with selected parameters. For instance, the method may comprise instructing the user to select a working range of at least one parameter selected from pH, optical density, and light scattering and program the controller to direct the effective volume of the additive responsive to the at least one selected working range.

One exemplary embodiment of the systems and methods for pH calibration will be described with reference to FIG. 1. In more detail for a particular embodiment, referring to FIG. 1. The buffer calibration curve may be generated using a calibration apparatus 10 to generate the pH vs. $CO_2$ calibration curve. The apparatus may comprise an air pressure regulator 10 having an input port 11 and an output port 12; a $CO_2$ pressure regulator 20 having an input port 21 and an output port 22; a first flow restrictor 30, optionally tunable, having an input port 31 and an output port 32; a second flow restrictor 40, optionally tunable, having an input port 41 and an output port 42; a first pressure sensor 50; a second pressure sensor 51; a calibration gas mixing 3-way solenoid switch 60, having a normally closed port 61, a normally open port 62, and a common port 63; a first 70, second 80, third 90, fourth 100, and fifth 110, gas mixing reservoir, each having an input port and an output port, a first 120, second 130, third 140, fourth 150, and fifth 160 port select 3-way solenoid switch, each having a normally closed port, a normally open port, and a common port; a first $CO_2$ sensor 170; a second $CO_2$ sensor 180; a calibration controller 190; and a computing system 250. The gas mixing reservoir may have an internal volume between 10 mL and 1 L, for example, between 40 mL and 60 mL. The $CO_2$ sensors may independently have a measurement range of 0% to 30% $CO_2$, for example, 0% to 10% $CO_2$. In the exemplary embodiment of FIG. 1, the first $CO_2$ sensor 170 has a measurement range of 0% to 10% $CO_2$ and the second $CO_2$ sensor 180 has a measurement range of 0% to 30% $CO_2$.

In an exemplary method performed with the system of FIG. 1, air may be supplied at a pressure higher than 3 psi to the input port 11 of the air pressure regulator 10. The output port 12 of the air pressure regulator 10 may be connected to the first pressure sensor 50 and the input port 31 of the first flow restrictor 30. The output port 32 of the first flow restrictor 30 may be connected to the normally open port 62 of the calibration gas mixing 3-way solenoid switch 60. $CO_2$ at a pressure higher than 3 psi may be supplied to the input port 21 of the $CO_2$ pressure regulator 20. The output port 22 of the $CO_2$ pressure regulator 20 may be connected to the second pressure sensor 51 and the input port 41 of the second flow restrictor 40. The output port 42 of the second flow restrictor 40 may be connected to the normally closed port 61 of the calibration gas mixing 3-way solenoid switch 60.

The first flow restrictor 30 and second flow restrictor 40 may be tuned such that the difference in flow between the first flow restrictor and second flow resistor is less than 10% when the pressure across the flow restrictors is approximately the same (for example, within 5%).

In the exemplary embodiment, the air pressure regulator 10 and $CO_2$ pressure regulator 20 may be set such that the regulated output pressures are between 1 psi and 10 psi, for example, between 3 psi and 4 psi.

The common port 63 of the calibration gas mixing 3-way solenoid switch 60 may be connected to the input port 71 of the first gas mixing reservoir 70. The output port 72 of the first gas mixing reservoir 70 may be connected to the common port 123 of the first port select 3-way solenoid switch 120. The normally closed port 121 of the first port select 3-way solenoid switch 120 may be connected to the input port 171 of the first $CO_2$ sensor 170 and the output port 172 of the first $CO_2$ sensor may be connected to the input port 181 of the second $CO_2$ sensor 180. The output port 182 of the second $CO_2$ sensor 180 may be connected to a bubbler 200. In the exemplary embodiment of FIG. 1, the bubbler 200 may be inserted into approximately 30 mL of the buffer fluid 210 in a 50 mL conical tube 220. Other buffer fluid volumes are also contemplated such as volumes between 10 mL and 40 mL of fluid. Other containers are also contemplated such as test tubes, or flasks. For containers with larger volumes, larger volumes of buffer fluid may be used, such as volumes between 40 mL and 500 mL. However, these volumes are exemplary. The disclosure is not limited to such volumes.

In exemplary FIG. 1, the bubbler 200 contains a check valve to prevent liquid flow back to the $CO_2$ sensors 170, 180 and an opening where gas is bubbled into the buffer fluid. The input ports 81, 91, 101, 111, of the second 80, third 90, fourth 100, and fifth 110 gas mixing reservoirs may be connected to four female luer lock connectors. The common ports 133, 143, 153, 163 of the second 130, third 140, fourth 150, and fifth 160 port select 3-way solenoid switches may be respectively connected to the output ports 82, 92, 102, 112 of the second 80, third 90, fourth 100, and fifth 110 gas mixing reservoirs. The normally closed ports 131, 141, 151, 161 of the second 130, third 140, fourth 150, and fifth 160 port select 3-way solenoid switches may be connected to the input port 171 of the first $CO_2$ sensor 170. By configuring a single port select 3-way solenoid switch so the common port of the selected switch was connected to the normally closed port, a single port may be selected to be connected to the first $CO_2$ sensor 170 and the $CO_2$ concentration of a gas source connected to one of the input ports 81, 91, 101, 111 of the second, third, fourth, or fifth gas mixing reservoirs may be measured and/or controlled.

In the exemplary embodiment of FIG. 1, the gas connections may be made with tubing such as C-flex tubing, PVC tubing, or urethane tubing. Generally, tubing and components with low $CO_2$ permeability may be used.

In the embodiment of FIG. 1, the conical tube 220 may be inserted into a dry block heater 230 to maintain the temperature of the buffer fluid 210 at approximately 37° C. A conventionally calibrated pH sensor electrode 240 may be inserted into the conical tube to measure the pH of the buffer fluid inside the tube using a pH meter 241.

In operation of the exemplary embodiment of FIG. 1, $CO_2$ gas mixtures may be generated by cycling the gas mixing 3-way solenoid switch 60 with a period between 1 second and 10 seconds, for example, 4 seconds, and varying the duty cycle, or percentage of the period where the normally closed port 61 is connected to the common port 63. When the duty cycle is set to 1%, the $CO_2$ percentage at the output 72 of the first gas mixing reservoir 70 may be approximately 1%. Other methods of generating the gas mixture are within the scope of the disclosure. In some embodiments, one or more gas mixture may be provided having the selected $CO_2$ concentration. The $CO_2$ gas mixture may have a concentration between about 1% and about 100%, for example, between about 1% and about 30%.

In the exemplary embodiment of FIG. 1, the first port select 3-way solenoid switch 120 may be configured to connect the common 123 and normally closed port 121 of the first port select 3-way solenoid switch 120.

In the exemplary embodiment of FIG. 1, to generate a calibration curve, duty cycles of 0, 1, 2, 4, 8, 12, 16, 25, and 100 percent $CO_2$ may be generated sequentially. It should be noted that these duty cycles and $CO_2$ concentrations may be selected for general bicarbonate buffered cell culture media. However, other duty cycles and $CO_2$ concentrations may be selected for different buffering capacities or buffer systems.

Each duty cycle may be set until the pH reading of the pH electrode determined by a pH meter 241 is stable and does not change by more than a threshold over a stable period. The threshold may be, for example, 0.01 pH units, although other thresholds between 0.001 and 0.05 or 0.1 units may be used. The stable period may be, for example, 1 minute, although other stable periods between 10 seconds and 30 minutes may be used. When the pH meter 241 reading is stable, the pH reading may be recorded along with the measured $CO_2$ percentage to generate a pH and $CO_2$ percentage pair data set. When all of the pH vs. $CO_2$ percent pairs are generated, the measured data may be used to determine the best fit parameters A, B, and C that result in the buffer formula having the lowest least squares error with the measured data, using standard numerical methods such as the Levenberg-Marquardt algorithm.

Data from the pressure sensors 50, 51, $CO_2$ sensors 170, 180, and pH meter may be obtained by the controller 190 and related computing system 250 connected to the calibration apparatus 1. The 3-way solenoid switches may each be individually activated by a signal from the controller 190, for example, in response to commands from the computing system 250. The execution of calibration curve generation steps, including setting of the gas-mixing 3-way solenoid switch 60 duty cycle, calculation of the stability criteria, and determination of the best fit parameters for the buffer formula, may be performed by the controller 190, optionally by a related computing system 250.

In the exemplary embodiment of FIG. 1, where the conical tube 220 is maintained at 37° C. and gas is bubbled through the buffer fluid 210, there may be loss of water due to evaporation. Observed evaporation rates in a test run were approximately 200 μL per hour, and generally in the range of between about 150 μL per hour and 250 μL per hour. It is noted that evaporation may result in a pH error, for example, up to approximately 0.03 units.

To compensate for evaporation, water, buffer, or another solution may be introduced into the conical tube 220 at a rate approximately matching a measured evaporation rate using methods known in the art. For example, a syringe pump 260 may be configured to deliver the make-up fluid. In the exemplary embodiment of FIG. 1, syringe pump 260 may be configured to delivery 180 uL of water to the conical tube 220 through tubing 261 to compensate for evaporation.

Figure 2:
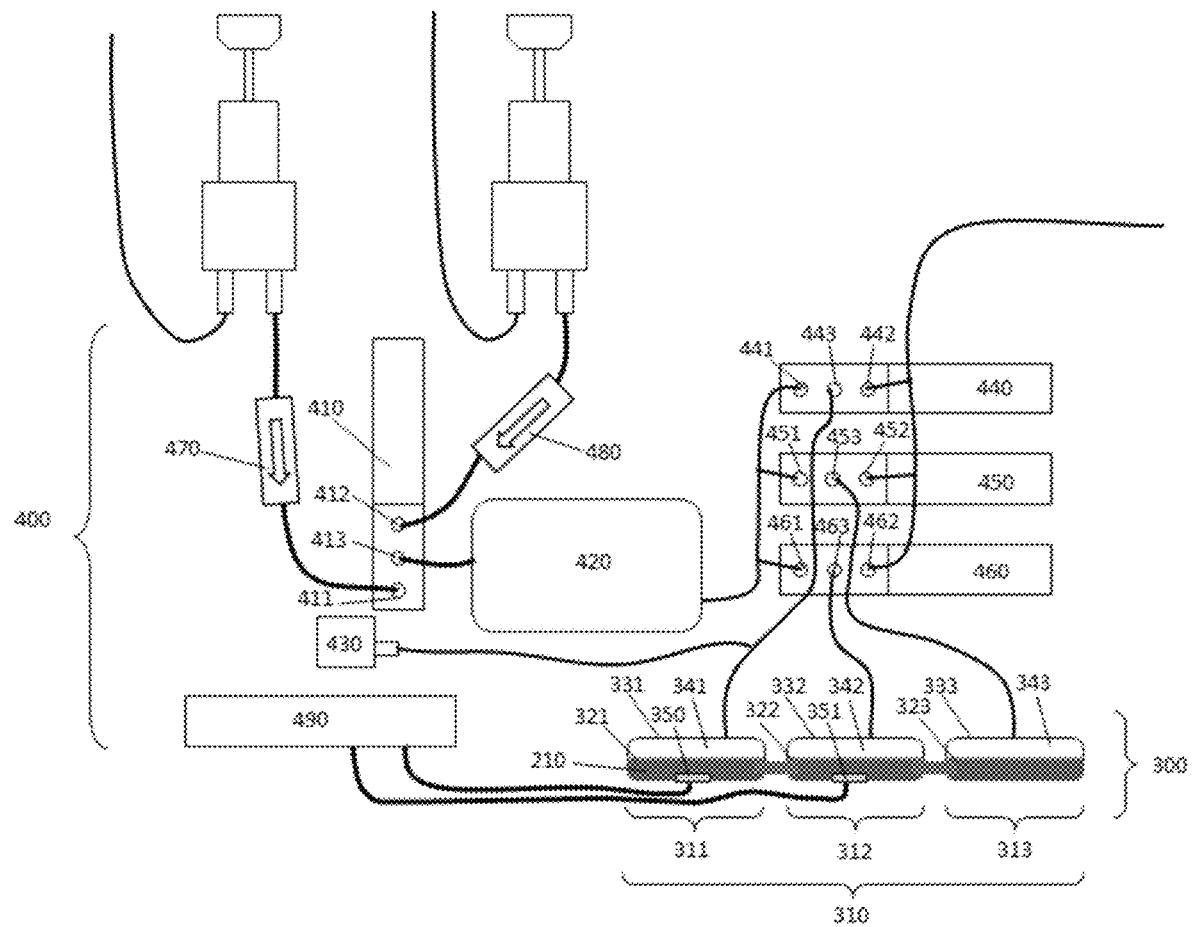
FIG. 2 is a schematic diagram of a system, according to one embodiment.

Referring now to the exemplary embodiment shown in FIG. 2, the pH sensor calibration curve may be generated in a microbioreactor device 300.

In some embodiments, the microbioreactor 300 may be of a type similar in structure to devices described in U.S. Patent Application Publication No. 2015/0132845, and U.S. Pat. No. 9,574,167, each of which is herein incorporated by reference in its entirety for all purposes. The microbioreactor 300 of FIG. 2 comprises a growth chamber 310 containing a first 311, second 312, and third 313 sub-chamber, each with a reconfigurable volume and in fluid communication with each other. Each sub-chamber may comprise a flexible member 321, 322, 323 and a retaining structure 331, 332, 333. The retaining structure and the flexible member of each sub-chamber may form an upper-chamber 341, 342, 343 opposite each sub-chamber where the gas pressure in the upper-chamber controls the deflection of the flexible member over each sub-chamber, which changes the volume of each sub-chamber.

The flexible member may be made from a material permeable to gasses such as oxygen and $CO_2$. One exemplary material is silicone. However, other materials are within the scope of the disclosure.

By alternately pressurizing the upper chambers for the three sub-chambers, fluid transfer between sub-chambers may be accomplished to provide fluid mixing and also gas transfer between the upper chamber gas and the buffer fluid. The microbioreactor growth chamber may also comprise a first 350 and second 351 optical pH sensors which comprise a pH sensitive dye.

In the exemplary embodiment of FIG. 2, the buffer fluid 210 may be introduced into the microbioreactor device in a way so there are substantially no air bubbles. The volume of the buffer fluid may be equal to the maximal volume of two sub-chambers, for example, approximately 2 mL.

In the exemplary embodiment of FIG. 2, the controller for the microbioreactor 400 may be operatively connected to a controller gas mixing 3-way solenoid switch 410 with a common port 413, a normally closed port 411, and a normally open port 412, a controller gas mixing reservoir 420, a controller pressure sensor 430, and a first 440, second 450, and third 460 mixing 3-way solenoid switch, each comprising a common 443, 453, 463, normally open 442, 452, 462, and normally closed port 441, 451, 461. The normally closed port 411 of the controller gas mixing 3-way solenoid switch may be connected, through a first controller check valve 470, to a regulated pressure of $CO_2$, for example, at approximately 3 psi. The normally open port 412 of the controller gas mixing 3-way solenoid switch 410 may be connected, through a second controller check valve 480, to a regulated pressure of air, for example, at approximately 3 psi. The first 470 and second 480 controller check valves may be arranged to prevent gas flow back to the source of $CO_2$ pressure and the source of air pressure.

The common port 413 of the controller gas mixing 3-way solenoid switch 430 may be connected to a controller gas mixing reservoir 420. The normally closed ports 441, 451, 461 of the first 440, second 450, and third 460 mixing 3-way solenoid switches may be connected to the controller gas mixing reservoir 420, the normally open ports 442, 452, 462 of the first 440, second 450, and third 460, mixing 3-way solenoid switches may be connected to an external $CO_2$ sensor, and the common ports 443, 453, 463 of the first 440, second 450, and third 460 mixing 3-way solenoid switches may be connected, respectively, to the upper-chamber 341, 342, 343 of the first 311, second 312, and third 313 sub-chambers. The first 440, second 450, and third 460 mixing 3-way solenoid switches may be configured such that the common port 443, 453, 463 of each mixing 3-way solenoid switch was alternately connected to the controller gas mixing reservoir 420 to pressurize the corresponding upper-chamber.

The exemplary system of FIG. 2 may be operated such that one upper-chamber at a time may be connected to the controller gas mixing reservoir for a time ranging between 0.2 and 1 second, for example, about 0.33 seconds, in a periodic pattern where the first upper-chamber 341 is pressurized, then the second upper-chamber 342 is pressurized, then the third upper-chamber 343 is pressurized.

In any of the embodiments disclosed herein, a pressurization pattern may be maintained throughout the calibration procedure to continuously mix the buffer fluid and allow gas exchange between the upper chambers and the buffer fluid. For instance, the method may comprise pressurizing or otherwise agitating the buffer and gas mixture to produce the solution.

The controller pressure sensor 430 may be connected to the first upper-chamber 341 to measure pressure of the first upper chamber. The controller also comprises an optical sensor measurement apparatus 490, producing a signal from each optical pH sensor.

In one exemplary embodiment, the connection between the normally open ports 442, 452, 462 of the three mixing 3-way solenoid switches 440, 450, 460 may be connected to the $CO_2$ sensors 170, 180 in the calibration apparatus 1 through the second 130, third 140, fourth 150, or fifth 160 port-select 3-way solenoid switch after passing through the second 80, third 90, fourth 100, or fifth 110 gas mixing reservoir.

In one exemplary embodiment, the first 470 and second 480 controller check valve may have a cracking pressure less than 0.1 psig.

The buffer fluid in the microbioreactor may be sequentially equilibrated with four different concentrations of $CO_2$. In the exemplary embodiment of FIG. 2, the fluid was equilibrated by setting the duty cycle of the controller gas mixing switch to 0%, 100%. In any embodiment, two percentages may be selected to correspond to a pH on either side of an anticipated pH setpoint. More than four calibration points may be used if desired. Each duty cycle may be maintained until the signal from the two optical pH sensors is stable within a selected stability criterion.

Example stability criteria include: the signal from each optical pH sensor does not change more than 0.5% of the full scale range of the signal over 5 minutes; and the average signal from each optical pH sensor over 5 minutes does not change by more than the standard deviation of the signal over 5 minutes. Other stability criterion may be used.

When the stability criteria is reached, the signal for each pH sensor, S1, S2, S3, S4 may be recorded along with the $CO_2$ percentage measured by the $CO_2$ sensors, and the pressure measured by the controller pressure sensor. After reaching the stability criteria for each duty cycle, the pH corresponding to each $CO_2$ percentage may be calculated and the resulting pH signal vs. pH data for each optical sensor may be used to determine the calibration parameters for each pH sensor.

To calculate the pH corresponding to each $CO_2$ percentage, the parameters A, B, and C previously determined may be used in the buffer calibration formula, as previously described. In certain embodiment, the value for $CO_{2perc}$ may be the measured $CO_2$ percentage when each stability criteria is reached, or a corrected $CO_2$ percentage that accounts for the pressure in the upper chambers. The corrected $CO_{2perc}$ may be calculated using the formula:

$$CO_{2corr}=(CO_{2perc})*(P)/(AP),$$

Where $CO_{2corr}$ is corrected $CO_2$ percentage, P is absolute pressure of the chamber during calibration, and AP is atmospheric pressure.

In the exemplary embodiment of FIG. 2, to determine the calibration parameters for each sensor, the four calculated pH values and the four corresponding pH sensor signals may be used to determine the best fit W, X, Y, Z parameters using the calibration formula as previously described and standard numerical methods such as the Levenberg-Marquardt algorithm.

In one test run using the exemplary system of FIG. 2, evaporation from the microbioreactors was observed to be approximately 20 µL per hour. To compensate for evaporation, a method as described in U.S. Patent Application Publication No. 2015/0132845, incorporated herein by reference for all purposes, may be used.

It should be noted that the methods may be employed for calibration of multiple pH sensors simultaneously. The multiple pH sensor calibration may involve a larger data set.

When multiple pH sensor are being calibrated simultaneously, a controller for each sensor is configured to regulate $CO_2$ pressure and/or air pressure from the same pressure regulators, the method may comprise synchronizing the calibration, such that the stability criteria may be reached for all reactors before continuing introducing another volume of gas mixture. Synchronization may provide stable gas mixtures and improved calibration performance.

In the exemplary embodiment of FIG. 2, the calibration method steps, including setting of the controller gas-mixing 3-way solenoid switch 410 duty cycle, calculation of the pH corresponding to each measured $CO_2$ percentage, accounting for the correction due to pressure in the microbioreactor upper chambers, calculation of the stability criteria, and determination of the best fit parameters for the calibration formula, may be performed by a controller and/or computing system 250. In some embodiments, the controller 190 may provide computing. In other embodiments, a computing system 250 may be in communication with the controller 400 such that commands and signals may be sent and acquired for processing.

Optical sensor measurement apparatus 490 may be used to acquire the signal from each pH sensor. The method may comprise selecting the appropriate apparatus for the particular optical pH sensor being used.

Figure 3:
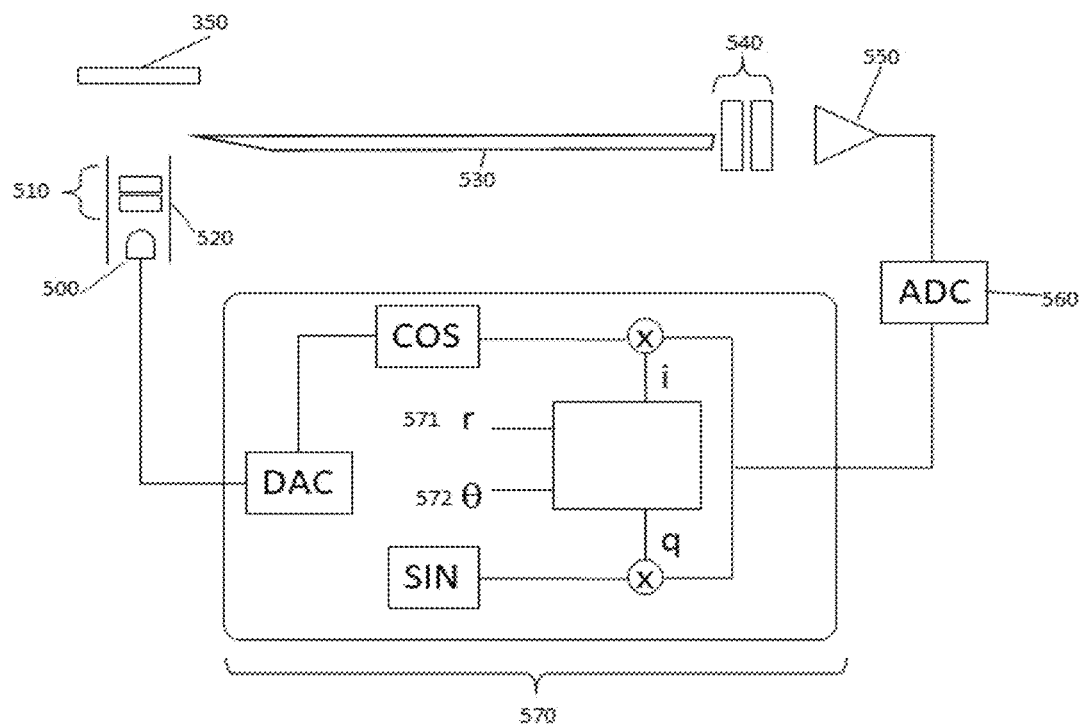
FIG. 3 is a schematic diagram of a system, according to one embodiment.

Referring now to FIG. 3, for each optical pH sensor 350, a sinusoidally modulated excitation LED 500 may be optically filtered with a short pass optical filter assembly 510 comprising one or more optical filters, to prevent light in the range of the optical pH sensor emission wavelengths from exciting the optical pH sensor. The sinusoidally excited and filtered light from the excitation LED may be directed towards the optical pH sensor 350 through an optical conduit 520. The optical emission from the pH sensor may be collected by an optical waveguide 530 and directed toward a long pass optical filter assembly 540 that prevents the wavelengths of light from the excitation LED from passing through to a photoreceiver circuit 550.

In some embodiments, the long pass optical filter assembly may include a low fluorescence interference filter. The photoreceiver circuit 550 may condition the optical signal emitted from the optical pH sensor 350 into an electrical signal which is subsequently converted into a sequence of 16-bit numbers using an analog to digital converter 560. The sequence of numbers may be processed by a vector analyzer algorithm 570 known in the art to determine the magnitude and phase of the received optical pH sensor signal with respect to the LED excitation. The magnitude 571 and phase 572, or phase 572 may be the processed signal from each pH sensor 350 used in the pH sensor calibration procedure.

Figure 4A:
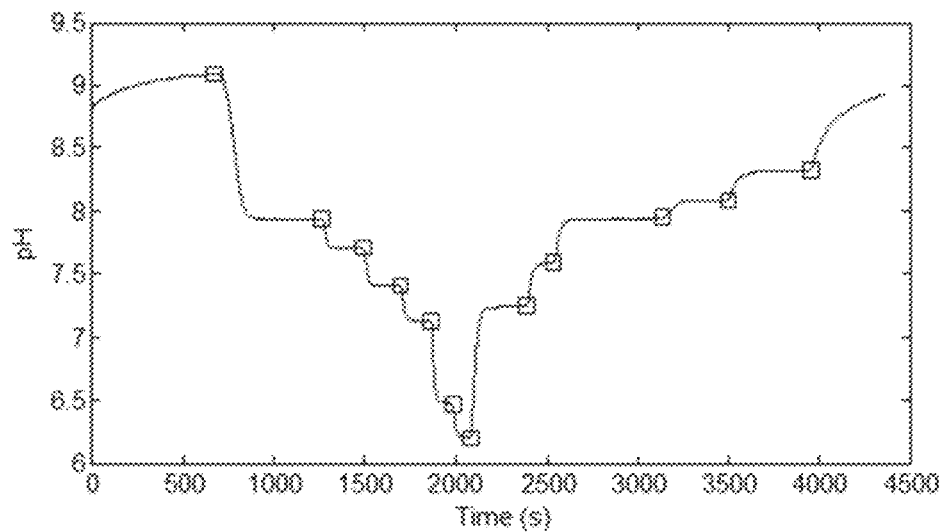
FIG. 4A is a graph of pH over time, according to one embodiment.
Figure 4B:
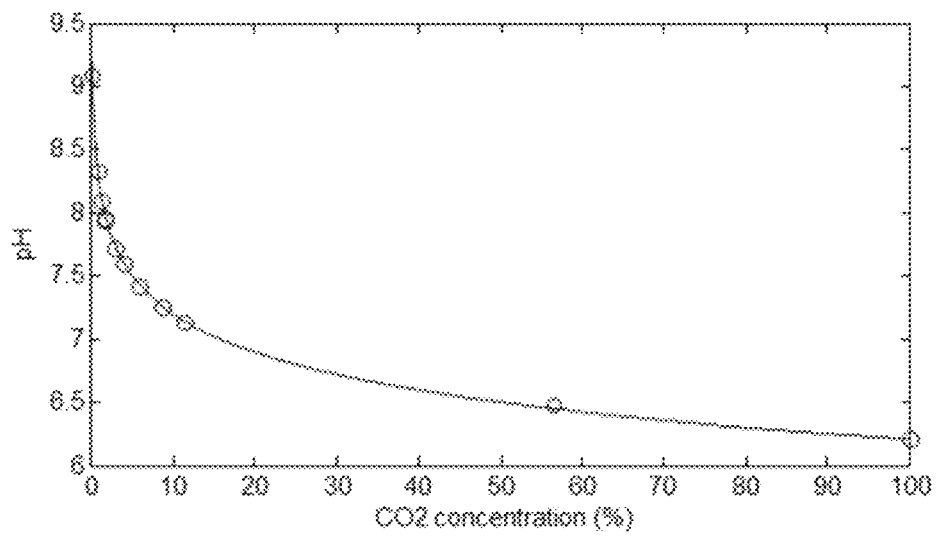
FIG. 4B is a graph of pH over measured $CO_2$ concentration, according to one embodiment.

The graph of FIG. 4A shows pH vs. time measured by the pH electrode and pH meter in an exemplary test run of the systems disclosed herein. The graph of FIG. 4B shows pH vs. measured $CO_2$ concentration with the best fit buffer calibration curve, where A=6.199, B=−1, and C=0. In the exemplary test run, the buffer liquid was 1.8 g/L of sodium bicarbonate.

Figure 5A:
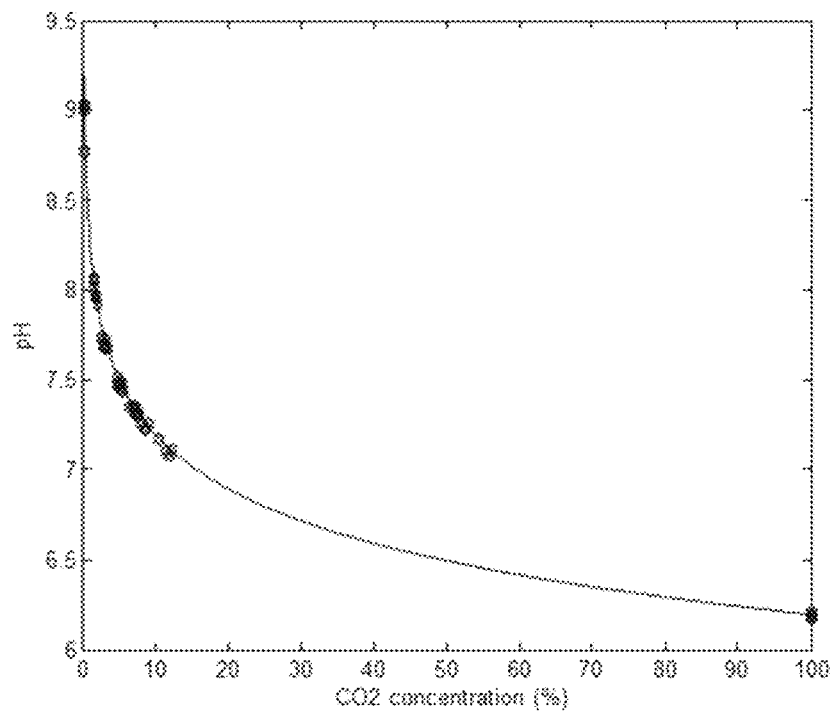
FIG. 5A is a graph of pH over measured $CO_2$ concentration, according to one embodiment.
Figure 5B:
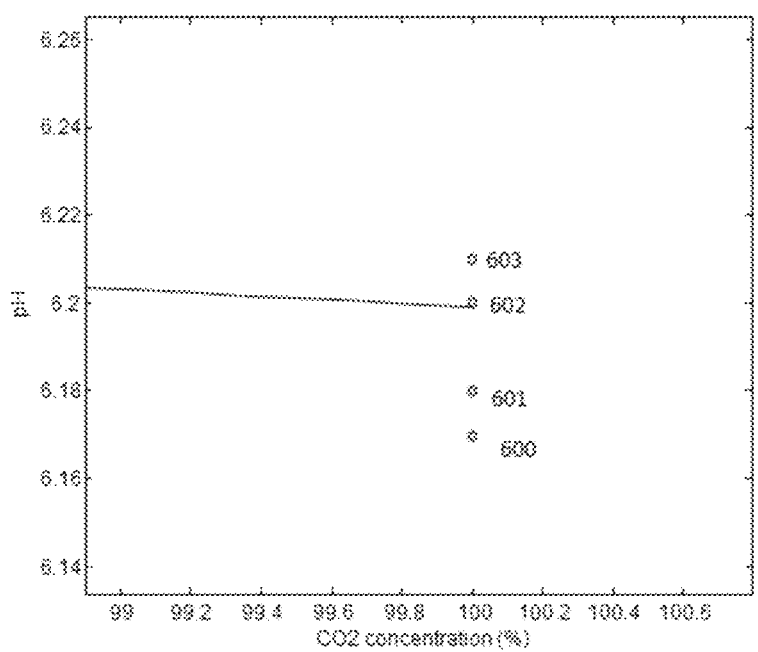
FIG. 5B shows a zoomed in portion of the graph of FIG. 5A.

The graph of FIG. 5A shows four repeated measurements of the pH vs. $CO_2$ percentage curve. The graph of FIG. 5B shows a zoomed in portion of the graph of FIG. 5A at 100% $CO_2$, where the first 600, second 601, third 602, and fourth 603 points are shown. The data are consistent with evaporation as the buffer liquid becomes concentrated with evaporation. In the exemplary test run, the buffer was 1.8 g/L sodium bicarbonate.

Figure 6:
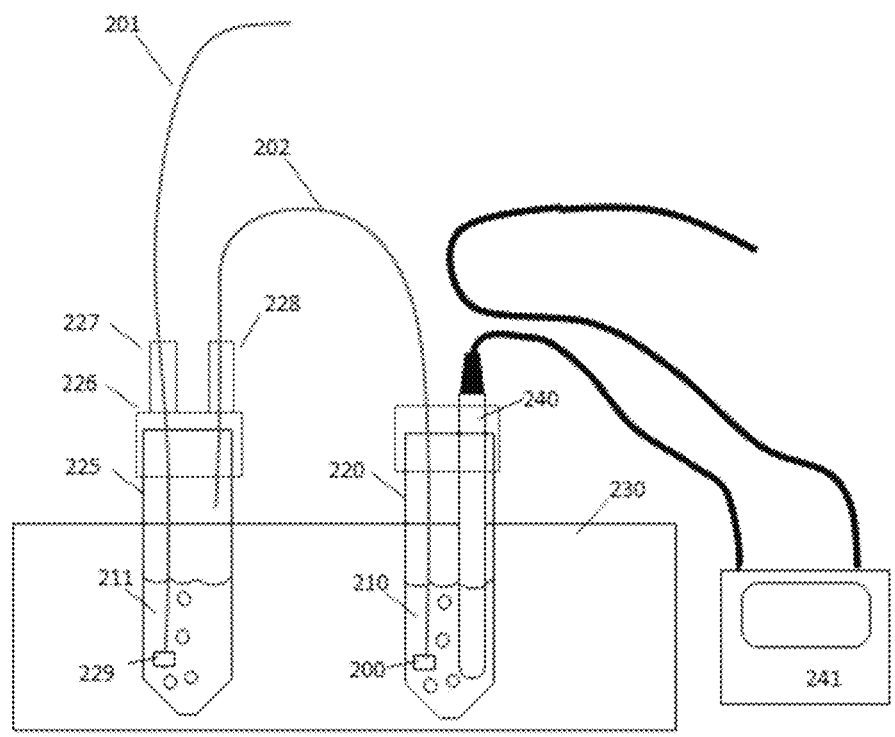
FIG. 6 is a schematic diagram of a system, according to one embodiment.

Referring specifically to FIG. 6, one method to compensate for evaporation loss during generation of the buffer calibration curve is to use a humidification conical tube 225 filled with a volume of a humidification solution 211, such as a saline solution, with a similar salinity as the buffer solution 210. In the exemplary embodiment, the volume of the humidification solution 211 may be similar to the volume of the buffer solution 210.

The humidification conical tube 225 may be sealed with a cap with two ports 226 and placed in the same heater block 230 as the conical tube 220 with buffer solution 210. The gas from the calibration apparatus 1 may be directed into the bubbler port 226 connected to a humidification bubbler 229, so the gas is also bubbled through the humidification solution 211. The humidified gas may then exit the humidification conical tube 225 through an output port 228 connected to the bubbler 200 in the buffer solution 210 through a length of tubing 202.

Thus, in some embodiments, the temperature control subsystem may be configured to control temperature of the humidification solution.

In a test run with the exemplary system of FIG. 6, because the salinity of the humidification solution 211 was similar to the salinity of the buffer solution 210, the evaporation rates for the humidification solution 211 and buffer solution 210 were similar. The evaporation loss of the buffer solution 210 was minimized during the generation of the buffer calibration curve.

EXAMPLES

The function and advantages of these and other embodiments can be better understood from the preceding exemplary embodiments and following examples. The examples are intended to be illustrative in nature and are not considered to be limiting the scope of the invention.

Example 1

Calibration of a pH Sensor

In a test run, pH sensors inside a microbioreactor were calibrated using the disclosed method.

A solution of 1.8 g/L of sodium bicarbonate and 6.92 g/L sodium chloride in deionized water was prepared as an example culture medium or calibration solution.

A solution of 8 g/L sodium chloride in deionized water was prepared as a humidification solution.

Generally, the concentration of sodium chloride in the humidification solution was selected to be within 1 g/L of the calibration solution, to match the evaporation rate of the humidification solution and the calibration solution.

A dry block heater with insert for 50 mL conical tubes was pre-heated to 38° C. A pH probe (distributed by Oakton® Instruments, Vernon Hills, IL) was connected to a pH meter (Oakton® Instruments). The pH probe was calibrated using a series of standard calibration buffers.

A media characterization assembly was prepared by connecting a humidification tube assembly with a pH probe tube assembly.

The humidification tube assembly was constructed using a 50 mL conical tube and a cap assembly with two barbs, one barb where gas was introduced to the 50 mL conical tube and one barb where humidified gas exited from the 50 mL conical tube. The barb where gas was introduced to the conical tube was connected to a dip tube such that the introduced gas would bubble through liquid in the conical tube.

The pH probe tube assembly was constructed using a 50 mL conical tube and a cap with two holes. A first hole, with 3/16 inch diameter was used to allow insertion of a dip tube attached to an input gas tube such that gas introduced into the input gas tube bubbled through the solution in the conical tube. A second hole, with ½ inch diameter allowed insertion of the pH probe.

The barb of the humidification tube where the humidified gas exited the humidification tube assembly was connected to the input gas tube of the pH probe tube assembly.

The humidification tube assembly was filled with 20 mL of humidification solution and the pH probe tube assembly was disinfected with alcohol before filling with 15 mL of the calibration solution. The pH probe was disinfected with alcohol and inserted into the second hole of the pH probe tube assembly such that the end of the pH probe was immersed in the calibration solution. The barb where gas was introduced to the humidification tube was connected to a mixed gas outlet of a $CO_2$ gas mix generator.

The $CO_2$ gas mix generator contained a $CO_2$ inlet, an air inlet, a $CO_2$ pressure regulator, an air pressure regulator, a $CO_2$ flow resistance, an air flow resistance, a $CO_2$ check valve, an air check valve, a gas mixing switch, a gas mixing reservoir, a first $CO_2$ sensor with 0-10% range, a second $CO_2$ sensor with a 0-30% range, an air pressure sensor, a $CO_2$ pressure sensor, a mixed gas outlet, and a controller.

The $CO_2$ inlet was connected to an input port of the $CO_2$ pressure regulator, the air inlet was connected to an input port of the air pressure regulator. An output port of the $CO_2$ pressure regulator was connected the $CO_2$ pressure sensor and to an input side of the $CO_2$ flow resistance; an output side of the $CO_2$ flow resistance was connected to the input side of the $CO_2$ check valve; an output side of the $CO_2$ check valve was connected to a normally closed port of the gas mixing switch.

The air inlet was connected to an input port of the air pressure regulator, the air inlet was connected to an input port of the air pressure regulator. An output port of the air pressure regulator was connected to the air pressure sensor and an input side of the air flow resistance; an output side of the air flow resistance was connected to the input side of the air check valve; an output side of the air check valve was connected to a normally open port of the gas mixing switch.

A common port of the gas mixing switch was connected to an input port of the gas mixing reservoir; an output of the gas mixing reservoir was connected to an input port of the first $CO_2$ sensor; an output port of the first $CO_2$ sensor was connected to the input port of the second $CO_2$ sensor; and an output port of the second $CO_2$ sensor was connected to the mixed gas outlet.

Gas mixtures with different partial pressure of $CO_2$ were generated by changing the duty cycle of the gas mixing switch using the controller. The gas mixing switch was operated with a 4 second period and the duty cycle was varied between 0% and 100%. The air pressure and $CO_2$ pressure were adjusted to approximately 4 psi and the air flow resistance and $CO_2$ flow resistance were selected to produce a gas flow rate of approximately 0.4 standard cubic feet per hour (SCFH).

The duty cycle of the gas mixing switch was sequentially set to 0%, 1%, 2%, 4%, 8%, 12%, 20%, 100%. For each duty cycle, the $CO_2$ partial pressure of the resultant gas mixture was recorded and the pH of the calibration solution with the gas bubbling through was measured every 4 seconds until the stability criterion was reached. An example stability criterion used was to measure that the pH value changed less than 0.01 for 15 minutes. When the stability criterion was satisfied, the $CO_2$ partial pressure and pH pair were recorded. The resultant $CO_2$ partial pressure and pH pairs for each of the above gas mixing switch duty cycles are shown in Table 1.

TABLE 1

Recorded pH and $CO_2$ Partial Pressure

| $CO_2$ % | pH |
|---|---|
| 0.019 | 9.08 |
| 0.956 | 8.07 |
| 1.777 | 7.81 |
| 3.435 | 7.53 |
| 6.844 | 7.23 |
| 10.448 | 7.06 |
| 17.611 | 6.83 |
| 100 | 6.08 |

The data from Table 1 was fit to a formula of the form:

$$pH_{fit} = A + B*\log_{10}(C + CO_{2perc}/100).$$

For the bicarbonate solution used in this example, the fitting parameters were:

A=6.0778,
B=−1.0009,
C=0.0008.

A microbioreactor (Erbi Biosystems, Inc., Woburn, MA) was filled to its 2 mL working volume with the calibration solution. The microbioreactor contained a first pH sensor, a second pH sensor, and three sub-chambers, each sub-chamber with a liquid side and a gas side, separated by a silicone membrane.

The liquid side of the sub-chambers were interconnected and the gas side of the three sub-chambers could be independently pressurized. Pressurization of the gas side of a sub-chamber inflated the silicone membrane, which displaced the liquid in the liquid side of the sub-chamber. By cycling the pressurization of the gas side of each sub-chamber, liquid was moved between sub-chambers, which resulted in mixing.

Over time because the silicone membrane was permeable to gasses such as oxygen and $CO_2$, the calibration liquid in the liquid side of the sub-chambers would equilibrate with the gas on the gas side of the sub-chambers and therefore, the dissolved gas composition of the calibration liquid was changed by changing the composition of the gas on the gas side of the sub-chambers.

The composition of the gas that pressurized the gas side of the sub-chambers was adjusted using a MBR gas mixing switch, where a normally closed port of the MBR gas mixing switch was connected to a source of $CO_2$ pressure set to approximately 4 psi and a normally open port of the MBR gas mixing switch was connected to a source of air pressure set to approximately 3.5 psi. A common port of the MBR gas mixing switch was connected to a microbioreactor gas mixing reservoir.

The gas side of each sub-chamber was pressurized and vented by using of a pressurization switch for each sub-chamber. The gas side of each sub-chamber was connected to a common port of its corresponding pressurization switch. The normally closed ports of each pressurization switch were all connected to the microbioreactor gas mixing reservoir and the normally open ports of each pressurization switch were all connected to a microbioreactor gas outlet. The microbioreactor gas outlet was connected to an input port of a $CO_2$ sensor box to measure the $CO_2$ composition of the gas (mixing gas) that equilibrated with the calibration liquid inside the microbioreactor.

Four gas mixtures were chosen to generate a calibration curve for the optical pH sensors. Approximately 0% $CO_2$, 9.4% $CO_2$, 28% $CO_2$, and 100% $CO_2$. For each target $CO_2$ concentration, the MBR gas mixing switch duty cycle set to 0% for the 0% $CO_2$ gas mixture and 100% for the 100% $CO_2$ gas mixture. For the 9.4% $CO_2$ and 28% $CO_2$ gas mixtures, the duty cycle of the gas switch was reset periodically using the following algorithm. Starting from an initial estimate of the duty cycle, D1, that would achieve the desired $CO_2$ percent, the actual $CO_2$ percent in the mixing gas with the duty cycle set to D1 was measured. After the measured $CO_2$ percent stabilized, the variable $CO_2M$ was calculated as:

$CO_2M$=(the stabilized $CO_2$% measurement)/100

Then a parameter gamma was calculated as:

gamma=$(1-D1)/D1*CO_{2M}/(1-CO_2M)$

Then an updated duty cycle, D2 was calculated as:

D2=1/(gamma*(1−setpoint)/setpoint+1)

where the setpoint was calculated as:

setpoint=(the targeted $CO_2$ percentage)/100

After mixing with the MBR gas mixing switch set to the updated duty cycle, D2, the process was repeated and a further updated duty cycle was generated by measuring a new stabilized $CO_2$% measurement, setting D1 above equal to D2, calculating an updated gamma, and calculating an updated duty cycle.

The pH sensor signal was measured as a phase shift between an excitation light source and a measured emission from the pH sensor. The phase shift was calculated using standard phase sensitive signal processing methods. For each gas mixture, the pH sensor signals were monitored until they were stable and did not change by more than a chosen threshold (typically 0.005 radians). The stabilized pH sensor signal, stabilized $CO_2$ percent, and calculated pH corresponding to the stabilized $CO_2$ percent are shown in Table 2 for the first pH sensor and Table 3 for the second pH sensor.

TABLE 2

Stabilized pH Sensor Signal, Stabilized
$CO_2$ Percent, and Calculated pH for sensor 1

| pH sensor phase | $CO_2$ % | Calculated pH |
|---|---|---|
| −0.1353 | 0.0574 | 8.94 |
| −0.569 | 100 | 6.08 |
| −0.349 | 9.8877 | 7.08 |
| −0.4548 | 26.9131 | 6.65 |

TABLE 3

Stabilized pH Sensor Signal, Stabilized
$CO_2$ Percent, and Calculated pH for sensor 2

| pH sensor phase | $CO_2$ % | Calculated pH |
|---|---|---|
| −0.0638 | 0.0574 | 8.94 |
| −0.5184 | 100 | 6.08 |
| −0.2512 | 9.8877 | 7.08 |
| −0.3754 | 26.9131 | 6.65 |

Where the calculated pH values were derived from the previously determined fit:

$$pH_{fit} = 6.0778 - 1.0009 * \log_{10}(0.0008 + CO_{2perc}/100)$$

For the final step of calibration, pH calibration parameters, W, X, Y, Z were determined for the two pH sensors by using the Levenberg-Marquardt algorithm to fit the measured pH sensor phase and calculated pH values with the formula:

$$pH_{sensor} = (\log_2(S-W) - \log_2(X-S)) * Y + Z$$

where S is the measured pH sensor phase.

The resulting parameters for the first and second sensor are shown in Table 4.

TABLE 4

Calculated pH Sensor Calibration Curve Parameters

|   | First pH sensor | Second pH sensor |
|---|---|---|
| W | −0.67721005 | −0.6367339 |
| X | −0.12160123 | −0.0573212 |
| Y | 0.38919387 | 0.3395566 |
| Z | 6.87396274 | 6.7432609 |

The process outlined above was repeated using various commercially available cell culture media instead of the bicarbonate solution with similar results.

Example fitting parameters for the pH vs. $CO_2$ parameters, A, B, C are shown in Table 5.

TABLE 5

Calculated Fitting Parameters for Cell Media

|   | 1.8 g/L bicarbonate | Media 1 | Media 2 |
|---|---|---|---|
| A | 6.0778 | 6.2131 | 6.3576 |
| B | −1.0009 | −0.891 | −0.8381 |
| C | 0.0008 | 0.0006 | 0.0007 |

Accordingly, the systems and methods disclosed herein may be employed to calibrate a pH sensor within an enclosed vessel, without sampling the fluid from the vessel.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure, and are intended to be within the scope of the invention. Accordingly, the foregoing description and drawings are by way of example only.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed.

The invention claimed is:

1. A method of calibrating a pH sensor fixed within an enclosed sterile vessel, comprising:
   introducing a buffer into the enclosed sterile vessel at a controlled temperature;
   sequentially introducing a plurality of gas mixtures, each gas mixture comprising $CO_2$, into the enclosed sterile vessel to form a plurality of gas mixture and buffer solutions having variable concentrations of $CO_2$;
   measuring a pH signal of each gas mixture and buffer solution in the enclosed sterile vessel with the pH sensor and a $CO_2$ concentration of a headspace gas of each gas mixture and buffer solution in the enclosed sterile vessel;
   calculating a pH value for each gas mixture and buffer solution in the enclosed sterile vessel from the $CO_2$ concentration with a first calibration curve for the buffer;
   calculating a calibration parameter for the pH sensor from the pH signal and the respective pH value for each gas mixture and buffer solution in the enclosed sterile vessel with a second calibration curve for the pH sensor; and
   automatically calibrating the pH sensor fixed within the enclosed sterile vessel with the calibration parameter.

2. The method of claim 1, wherein the plurality of gas mixture and buffer solutions is at least four gas mixture and buffer solutions, the method further comprising measuring the pH signal of each of the at least four gas mixture and buffer solutions and the $CO_2$ concentration of the headspace gas of the at least four gas mixture and buffer solutions in the enclosed sterile vessel, calculating at least four respective pH values, and calculating the calibration parameter for the pH sensor from the at least four pH signals and the at least four respective pH values.

3. The method of claim 1, comprising measuring the pH signal with the pH sensor and the $CO_2$ concentration after each solution of the plurality of gas mixture and buffer solutions reaches equilibrium.

4. The method of claim 1, further comprising generating the first calibration curve for the buffer.

5. The method of claim 4, wherein the first calibration curve for the buffer has a formula in the form of:

$$pH_{fit}=A+B*\log_{10}(C+CO_{2perc})$$

where A, B, and C are fitting parameters, $pH_{fit}$ is a fitted pH value as a result of fitting the pH signal to the first calibration curve, and $CO_{2perc}$ is the measured $CO_2$ concentration as a percentage of a total composition of the headspace gas.

6. The method of claim 5, wherein the controlled temperature is a first controlled temperature, the method further comprising:
calculating the fitting parameters A, B, and C by
sequentially introducing a stable mixture of $CO_2$ and air into the buffer at a second controlled temperature to form a stable mixture and buffer combination;
measuring a pH signal of the stable mixture and buffer combination and a $CO_2$ concentration of a headspace gas of the stable mixture and buffer combination;
fitting the pH signal of the stable mixture and buffer combination and the $CO_2$ concentration of the headspace gas of the stable mixture and buffer combination in the first calibration curve formula; and
determining the fitting parameters A, B, and C which produce lowest least squares error between the fitted pH value ($pH_{fit}$) and the measured pH signal of the stable mixture and buffer combination.

7. The method of claim 6, comprising measuring the pH signal of the stable mixture and buffer combination and the $CO_2$ concentration of the headspace gas of the stable mixture and buffer combination after the stable mixture and buffer combination reaches equilibrium.

8. The method of claim 1, wherein the second calibration curve for the pH sensor has a formula in the form of:

$$pH_{sensor}=(\log_2(S-W)-\log_2(X-S))*Y+Z,$$

where W, X, Y, and Z are fitting parameters and S is the pH signal.

9. The method of claim 8, further comprising:
calculating the fitting parameters W, X, Y, and Z by
fitting the pH signal and the pH value in the second calibration curve formula; and
determining the fitting parameters W, X, Y, and Z which produce lowest least squares error between the fitted pH value ($pH_{sensor}$) and the measured pH signal.

10. The method of claim 1, further comprising introducing a humidification solution into the enclosed sterile vessel in an amount effective to compensate for evaporation of the buffer.

11. The method of claim 1, wherein the buffer is controlled to a predetermined temperature between 30° C. and 39° C.

12. The method of claim 1, further comprising sterilizing the enclosed sterile vessel by at least one of steam sterilization, autoclave sterilization, gamma irradiation, e-beam irradiation, and ethylene oxide sterilization.

* * * * *